US008066978B2

(12) United States Patent
Cho et al.

(10) Patent No.: US 8,066,978 B2
(45) Date of Patent: Nov. 29, 2011

(54) BIOPOLYMER AND GENE COMPLEX

(75) Inventors: Myoung Haing Cho, Seoul (KR); Chong Su Cho, Seoul (KR)

(73) Assignee: Seoul National University Industry Foundation, Yangcheon-Gu, Seoul (KR)

( * ) Notice: Subject to any disclaimer, the term of this patent is extended or adjusted under 35 U.S.C. 154(b) by 980 days.

(21) Appl. No.: 11/571,890

(22) PCT Filed: Mar. 23, 2005

(86) PCT No.: PCT/KR2005/000839
§ 371 (c)(1), (2), (4) Date: Jan. 9, 2007

(87) PCT Pub. No.: WO2006/068346

PCT Pub. Date: Jun. 29, 2006

(65) Prior Publication Data

US 2007/0231270 A1 Oct. 4, 2007

(30) Foreign Application Priority Data

Dec. 24, 2004 (KR) ........................ 10-2004-0112043

(51) Int. Cl.
*A61K 31/74* (2006.01)
*C12N 15/00* (2006.01)
*C07H 21/02* (2006.01)

(52) U.S. Cl. .................. 424/78.31; 435/320.1; 536/23.1

(58) Field of Classification Search ............... 424/78.31; 435/320.1

See application file for complete search history.

(56) References Cited

FOREIGN PATENT DOCUMENTS

WO WO 99/13915 A1 3/1999

OTHER PUBLICATIONS

Kichler A., 2004, J. Gene Med., vol. 6, pp. S3-S10.*
Yin et al., 2008, Oncogene, vol. 27, pp. 5443-5453.*
Kim et al., Nov. 1, 2004, Canc. Res., vol. 64, pp. 7971-7976.*
Brognard et al., 2001, Canc. Res., vol. 61, pp. 3986-3997.*
Fajac et al., 2003, J. Gene Med., vol. 5. pp. 38-48.*
Li et al., 2003, World J. Gastroenterol., vol. 9(2), pp. 262-266.*
Rudolph et al., 'Jet nebulization of PEI/DNA polyplexes: physical stability and invitro gene delivery efficiency', J. Gene Med. Jan.-Feb. 2002, vol. 4(1), Abstract.
Morimoto et al., 'Molecular weight-dependent gene transfection activity of unmodified and galactosylated polyethyleneimine of hepatoma cells and mouse liver', Molecul. Ther. Feb. 2003, vol. 7(2), Abstract.
Kunath et al., 'Galactose-PEI-DNA complexes for targeted gene delivery: degree of substitution affects complex size and transfection efficiency', J. Controlled Release, 2003, vol. 88, Abstract.

* cited by examiner

*Primary Examiner* — Valarie Bertoglio
*Assistant Examiner* — David A Montanari
(74) *Attorney, Agent, or Firm* — Nixon Peabody LLP; Jeffrey L. Costellia

(57) ABSTRACT

Disclosed herein is a biopolymer/gene complex for the aerosol delivery of a gene. The biopolymer/gene complex comprises a polyethyleneimine (PEI) having a substitution of glucose for at least a portion of the primary amino groups of the polyethyleneimine, and the content of the polyethyleneimine is 2-4 times the content of the gene. Also, disclosed is a lung cancer therapeutic agent comprising a biopolymer/gene complex including a polyethyleneimine (PEI) having a substitution of glucose for 30-40 mol % of the primary amino groups of the polyethyleneimine, and a gene encoding PTEN, in which the content of the polyethyleneimine is 2-4 times the content of the gene.

8 Claims, 4 Drawing Sheets

[Fig. 1]
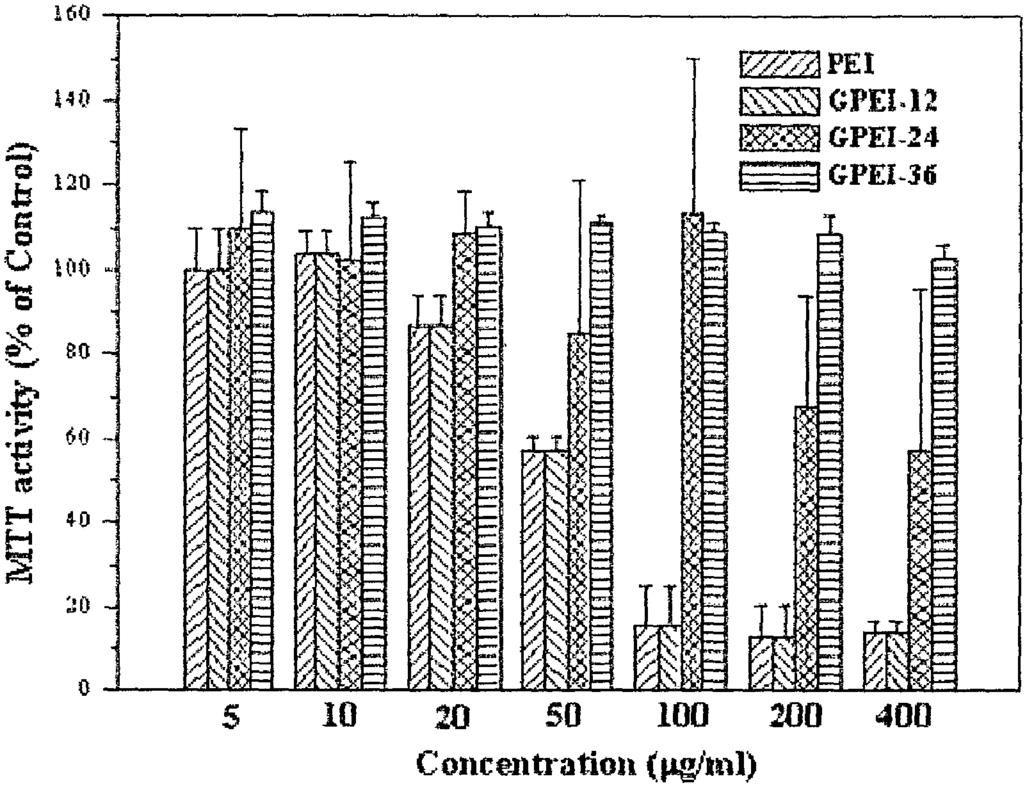
[Fig. 2]
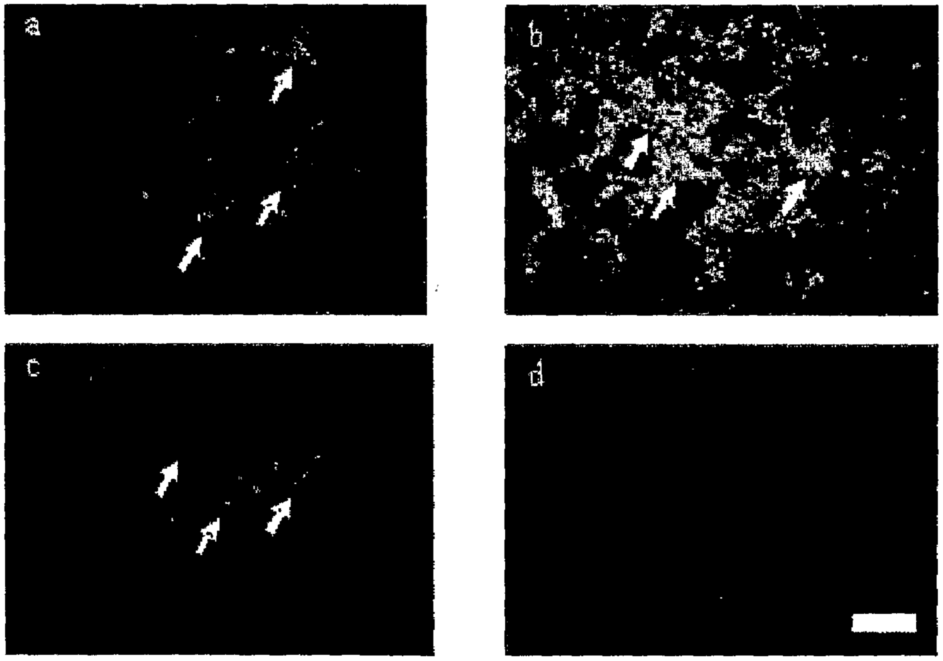

[Fig. 3]
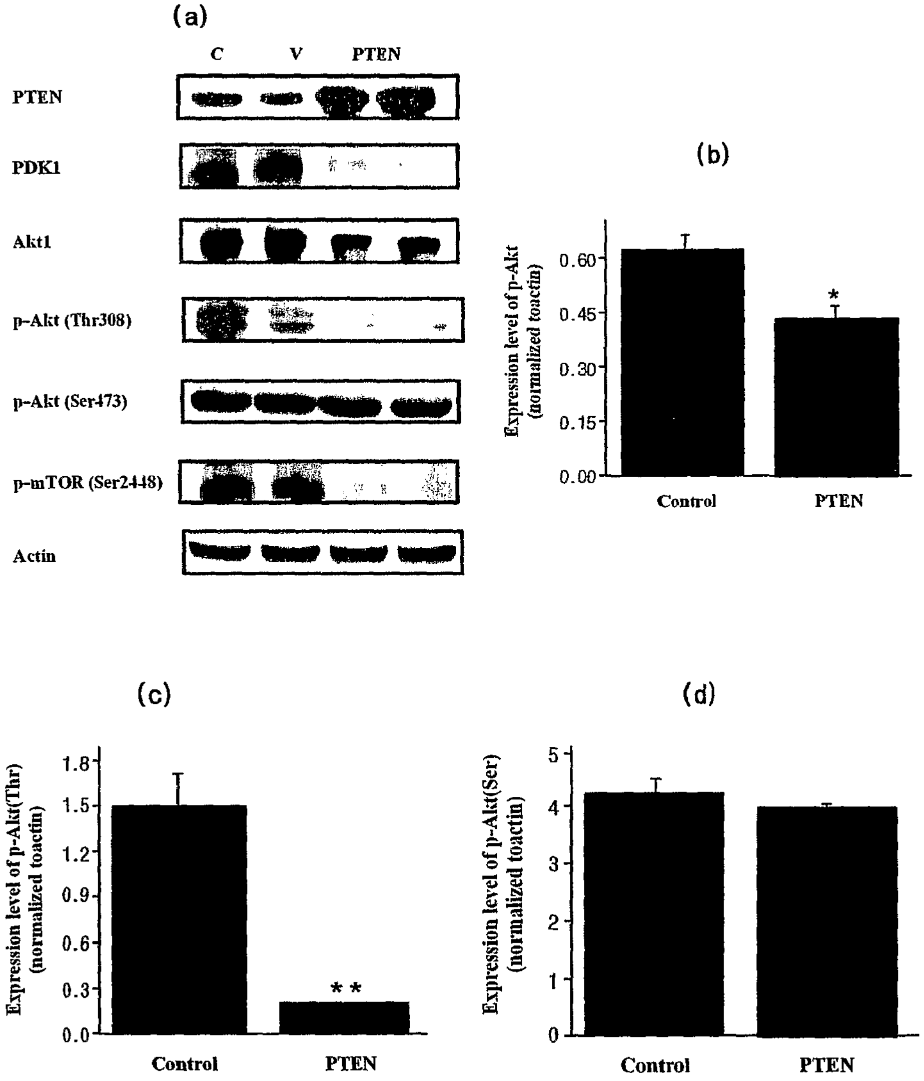
[Fig. 4]
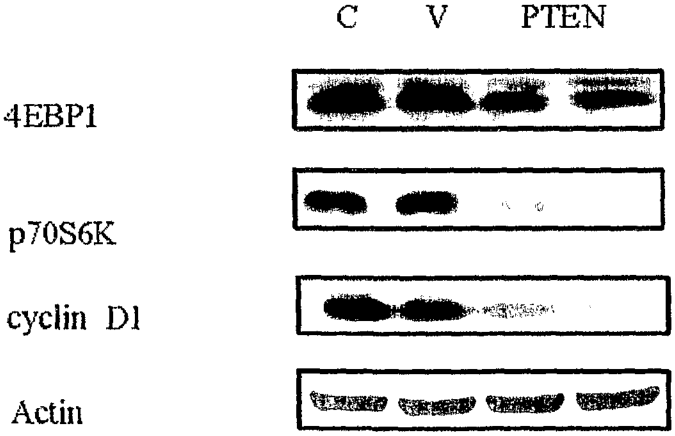

[Fig. 5]
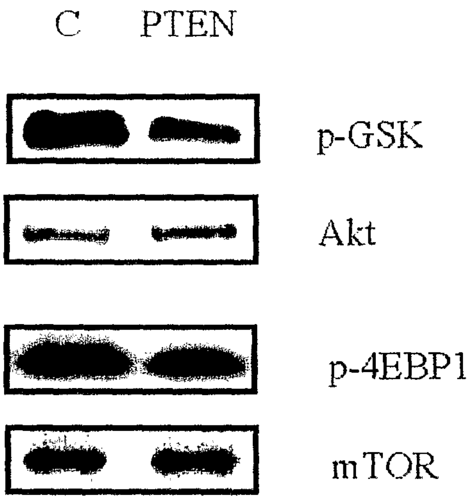
[Fig. 6]
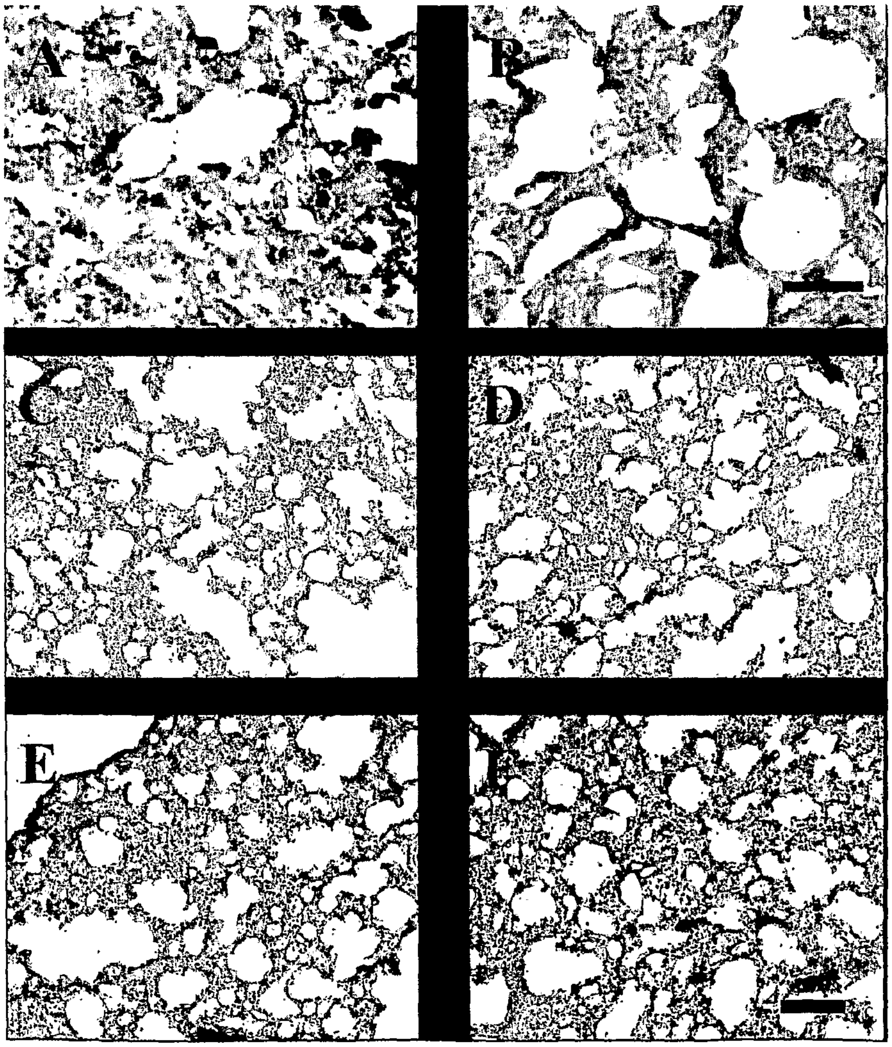

[Fig. 7]
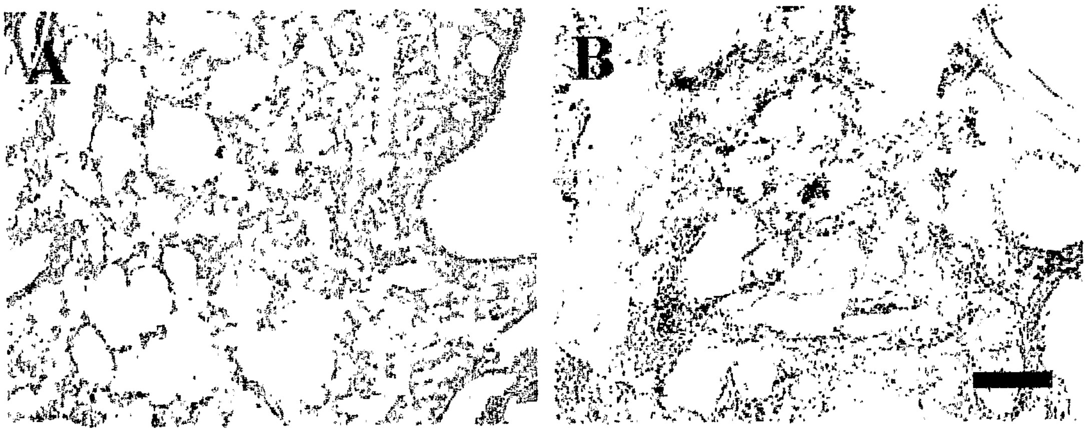

BIOPOLYMER AND GENE COMPLEX

The instant Application is a 371 of PCT/KR05/00839, filed on Mar. 23, 2005, which claims priority to Korean Application No. 10-2004-0112043, filed on Dec. 24, 2005.

TECHNICAL FIELD

The present invention relates to a biopolymer/gene complex, and more particularly, to a biopolymer/gene complex for the noninvasive aerosol delivery of a gene of interest.

BACKGROUND ART

Mutations of ras genes are found in about 30% of human tumors. The gene group consists of three kinds of families, including K-ras, N-ras, and H-ras, in which K-ras mutations are most frequently found in lung adenocarcinoma cells. Mice bearing such mutations demonstrate the most common histopathologic subtype of non-small cell lung cancer with short latency and high penetrance. Phosphatase and tensin homolog deleted on chromosome 10 hereinafter, referred to as "PTEN"), which catalyzes phosphorylation at the 3-position of the inositol ring phosphatidylinositol-3,4,5-triphosphate, is known as a tumor suppressor gene that suppresses the Akt signaling pathway to regulate the growth and survival of cells.

The fact has been known that Akt is activated in cancer cells by either activating the growth factor receptors of Ras or inactivating PTEN.

It was shown in recent reports that about 90% of non-small cell lung cancers are involved in the continuous activation of the PI3K/Akt pathway, and this activation of Akt promotes cellular survival and resistance to chemical therapy or γ-ray irradiation.

In addition, K-ras mutations can increase the activity of lung adenocarcinoma cells by the activation of Akt.

In view of such facts, a method of regulating the Akt is needed for the treatment of lung cancer.

Meanwhile, a method for the noninvasive delivery of genes by inhalation is known for the treatment of lung cancer.

Recombinant viral vectors have been used as effective gene delivery carriers because they have high affinity for airway epithelium and can be efficiently transfected into lung cells.

However, recombinant viral vectors, such as recombinant adenoviral vectors, have had limitations in their actual application because they have toxicity, cause immune response by repeated administration and are difficult to mass-produce.

Non-viral vectors have advantages in that they are easier to use than the viral vectors and cause less immune response. Furthermore, they also have the ability to be able to deliver high-molecular-weight DNA molecules.

Several recent studies have demonstrated that the binding of DNA with cationic polypeptides, such as polylysine, polyethylenimine (PEI), protamine, and histone, may be useful for gene delivery both in vivo and in vitro.

Among such polypeptides, PEI has received attention as a carrier for gene delivery because of its stability in an aerosol form. However, the use of PEI has been limited because of its strong toxicity caused by the characteristic accumulation of polycations.

Many researchers have studied possibilities for the direct delivery of various therapeutic agents into the lungs and the pulmonary lymph nodes by nebulization, and at the same time, attempted to use PEI as a gene therapy carrier, however, PEI has been reported to induce potential toxicity by accumulation.

Accordingly, in order to use polypeptides as gene delivery carriers, the following processes are necessarily required: adhesion to the cell surface endocytosis, isolation from endosomal lysosomal networks, migration into the cell nuclei, vector unpacking, and the like.

Therefore, there is a need for the development of an efficient and stable carrier for the aerosol delivery of a gene, which meets such requirements.

DISCLOSURE OF THE INVENTION

Technical Object

It is an object of the present invention to provide a biopolymer/gene complex.

Another object of the present invention is to provide a method for delivering the desired gene by the biopolymer/gene complex.

Still another object of the present invention is to provide a biopolymer/gene complex which can achieve effective aerosol delivery and has reduced toxicity.

Technical Solution

To achieve the above objects, in one aspect, the present invention provides a biopolymer/gene complex, in which the biopolymer comprises a polyethyleneimine (PEI) having a substitution of glucose for a portion of the primary amino groups of the polyethyleneimine, and the content of the polyethyleneimine is 2-4 times the content of the gene.

In another aspect, the present invention provides a lung cancer-therapeutic agent for aerosol delivery, which comprises a biopolymer/gene polymer including a polyethyleneimine (PEI) having a substitution of glucose for 30-40 mol % of the primary amino groups of the polyethyleneimine, and a gene encoding PTEN, in which the content of the polyethyleneimine is 2-4 times the content of the gene.

In still another aspect, the present invention provides a method for preparing a biopolymer/gene complex for the aerosol delivery of the desired gene, the method comprising: providing a biopolymer including a polyethyleneimine having a substitution of glucose for at least a portion of the primary amino groups of the polyethyleneimine and making the binding of the desired gene to the biopolymer in such a manner that the content of the polyethyleneimine is 2-4 times the content of the gene.

Advantageous Effects

According to the present invention, glucose is properly bound to a biopolymer, so that an aerosol gene delivery system with improvements in not only the efficiency of delivery into cells and but also stability can be provided.

The delivery of PTEN by the aerosol delivery of the inventive biopolymer/gene complex can achieve the effect of suppressing PKD1to inhibit the Akt kinase activity, thus inhibiting the tumor activity.

The delivery of PTEN by the aerosol delivery of the inventive biopolymer/gene complex can achieve the effect of influencing not only the Akt pathway, including mTOR, but also mTOR-dependent eIF4E-BP1, thus effectively inhibiting the proliferation of lung cancer.

BRIEF DESCRIPTION OF THE DRAWINGS

FIG. 1 shows the results of MTT in vitro cytotoxicity tests conducted at varying concentrations of glucose substitutions (mol %).

FIG. 2 shows the results of immunohistochemical analysis for mouse alveolar macrophages and monocytes having the biopolymer/gene complex delivered thereon.

FIG. 3 shows the results of Western blot analysis for the Akt protein of cellular tissue, after the delivery of PTEN into the cellular tissue by the biopolymer/gene complex.

FIG. 4 shows the results of regulation of components involved in the Akt signaling pathway.

FIG. 5 shows the results of assays for the kinase activities of p-GSK, Akt, p-4EBP1 and mTOR.

FIG. 6 shows the results of immunohistochemical analysis for the phosphorylation of Akt.

FIG. 7 shows the results of TUNEL analysis.

BEST MODE

An aerosol delivery method, one of methods for the delivery of a targeted gene, is known as an efficient and noninvasive method for the delivery of the targeted gene, because it can apply the gene to large surface areas and avoid potential risks which can occur in administration by other routes.

The present invention provides the biopolymer/gene complex for applying a specific gene by the aerosol delivery method. Particularly, the biopolymer/gene complex according to the embodiment of the present invention was seen to be effective in treating lung cancer.

The biopolymer/gene complex according to the embodiment of the present invention may comprise a glycosylated biopolymer as the biopolymer and a gene encoding PTEN.

Accordingly, the biopolymer/gene complex according to the embodiment of the present invention can be exemplified by a glycosylated polyethyleneimine (hereinafter, referred to as "GPEI")/PTEN complex having a PTEN-encoding gene bound to GPEI.

Generally, the cytotoxicity of PEI is considered to be induced by the primary amino acids of PEI, which account for about 30% of the total amino acids.

GPEI is a PEI derivative obtained by substituting some portions of the primary amino groups of PEI with a glucose moiety so as to increase the hydrophilicity of PEI, thus reducing the potential toxicity of PEI.

Although there is no special limitation in the glycosylation degree of GPEI according to the embodiment of the present invention if it can achieve the effects of the present invention, the glucose substitution is preferably 30-40 mol %, and most preferably about 36 mol %.

Although the binding ratio of the biopolymer to the gene in the embodiment of the present invention is not specifically limited if it can achieve the effects of the present invention, the binding ratio of GPEI to the gene in the GPEI/gene complex is preferably 2-4:1.

An embodiment of the present invention for the treatment of lung cancer may comprise making the binding of a lung cancer-inhibiting gene to GPEI to prepare a complex of GPEI with the lung cancer-inhibiting gene, and delivering the complex by an aerosol delivery method. In this regard, PTEN may be used as the lung cancer-inhibiting gene.

Also, GPEI according to the embodiment of the present invention can show an enhancement in the activity to deliver a gene bound to GPEI.

This enhancement of the gene delivery activity is considered to be attributable to more effective polyplex unpackaging, altered endocytic trafficking of GPEI, and escape from alveolar macrophage attacks. In addition, the glucose molecule substituted for the primary amino groups of GPEI is thought to act to stimulate the GPEI-PTEN complex to be selectively absorbed into lung tumor cells. Positron emission tomography (PET) consists of imaging the distribution of fluorine 18 fluorodeoxyglucose (18F-FDG), an analog of glucose, which is accumulated in a larger amount in the majority of tumors than in normal tissue.

Meanwhile, Akt is a serine/threonine kinase which acts as an important mediator in signaling pathways causing the cell survival and proliferation. Akt requires the phosphorylation of Thr308 and Ser473 for complete activity. As can be seen from FIG. 3, the results of the aerosol delivery of a GEI/PTEN complex, one embodiment of the present invention, suggest that the phosphorylation of Thr308 greatly inhibits the expression level of Akt, whereas the phosphorylation of Ser473 has no effect on the expression level of Akt.

PDK1, the upstream kinase of Akt, is known to phosphorylate Thr308. However, the identity of kinase that phosphorylates Ser473 is not yet exactly known. Several test results support the presumption that phosphatidylinositol 3,4,5-triphosphate binding is critical for membrane localization and kinase activity.

Meanwhile, the protein levels of Akt downstream targets, i.e., 4EBP1 and p70S6K, are influenced by PTEN delivery. This result suggests that the inhibition of phosphorylation of Thr308 can regulate the Akt downstream targets. Recent reports indicate that PDK1 is a cytoplasmic nuclear-shuttling protein, and its nuclear translocation is regulated by the PI3K pathway. The nuclear localization of PDK1 is increased in PTEN-deficient cells, suggesting that PTEN gene delivery can absolutely influence the functions of the Akt signaling pathway.

PDK1 is known to contribute to antiapoptosis by the phosphorylation of Akt. The inhibition of Akt activity has been reported to induce apoptosis in a wide range of mammalian cells.

In addition, Akt is known to contribute to the progression of tumors by not only the activation of antiapoptosis signaling and proliferation but also the promotion of cell infiltration and blood vessel production.

From these facts, it can be expected that the delivery of PTEN by the aerosol delivery of the biopolymer/gene complex according to the embodiment of the present invention can achieve the effect of suppressing PDK1 to inhibit Akt kinase activity, thus inhibiting tumor activity.

Meanwhile, the downstream effectors of PTEN, such as PI3K, are known to regulate numerous downstream pathways resulting in various cellular processes, including cellular apoptosis, invasion, migration and growth.

An increase in PTEN-related proteins in the lungs of mice causes leads to significant functional consequences. Specifically, the overexpression of PTEN in cancer cells results in cell cycle arrest and cell death by the inhibition of PI3K.

Also, the inhibition of PI3K is known to greatly reduce the invasive capacity of bladder cancer.

Another potential downstream target of PTEN is the group of translation regulators, 4E-BPs. These proteins act as effectors of signaling pathways involved in growth and cellular stress by the phosphorylation of mTOR that reduces the affinity for eIF4E binding with these proteins.

Recent study results indicate that mTOR regulates cell cycle progression by its cell growth effectors, S6K1 and 4E-BP1/eIF4E, and this may suggest another mechanism where increased PTEN may alter cell growth in the K-ras null mouse model.

From these facts, it can be expected that the delivery of PTEN by the aerosol delivery of the biopolymer/gene complex according to the embodiment of the present invention can achieve the effect of influencing not only the Akt pathway including mTOR but also mTOR-dependent eIF4E-BP1, thus effectively inhibiting the proliferation of lung cancer.

Hereinafter, the present invention will be described in detail by Examples such that any person skilled in the art may easily practice the present invention. It is to be understood, however, that the present invention may be embodied in various different forms and are not limited to Examples.

Anti-eIF4E used in the inventive Examples was purchased from BD Biosciences (San Jose, Calif.), and anti-PDK1 was purchased from Upstate Biotechnology (Waltham, Mass.). Anti-PTEN, anti-phospho-mTOR, and anti-4E-BP1 were purchased from Cell Signaling Technology (Beverly, Mass.). Other antibodies used in Western blot analysis and immunohistochemical analysis were purchased from Santa Cruz Biotechnology (Santa Cruz, Calif.).

In the following Examples, quantification of Western blot analysis was performed by Multi Gauge ver 2.02 program (FUJI FILM). Phospho-Akt/total Akt ratios, normalized to actin, were calculated based on the results of Western blot analysis and compared using Student's t-test.

EXAMPLE 1

Preparation of GPEI and GPEI-DNA Complex

GPEI was prepared by reacting PEI (M.W. 25K) with cellobiose in the presence of cyanoborohydride.

To determine the optimal glucose substitution of GPEI, a MTT in vitro cytotoxicity assay was performed on A549 cells at varyinc concentrations of glucose substitutions (mol %) to evaluate the cell viability. As a result, GPEI with the optimal glucose substitution was obtained.

FIG. 1 shows the results of the MTT in vitro cytotoxicity assay performed at varying concentrations of sugar substitutions (mol %).

As can be seen from FIG. 1, GPEIs whose primary amino groups have been almost modified into secondary amino groups by reducing amination showed low cytotoxicy, and among them, GPEI with a glucose substitution degree of 36 mol % showed the lowest cytotoxicity. Thus, GPEI with a glucose substitution degree of 36 mol % was used for aerosol gene delivery in this Example.

1 mg of DNA was dissolved in distilled water. To the solution, the GPEI carrier was added dropwise so that DNA and the GPEI carrier were mixed with each other at a ratio of 1:2.67. The mixture was supplemented with distilled water to a final volume of 50 ml.

Then, the mixture was allowed to react at room temperature for 30 minutes, thus preparing a GPEI/DNA complex. pcDNA3.1-GFP used as DNA in Example 1 was purchased from Invitrogen (Carlsbad, Calif.), and pcDNA3.0-PTEN was provided from Dr. Whang (UNC at Chapel Hill).

Then, to examine the aerosol delivery efficiency of the GPEI/DNA complex, immunohistochemical staining was performed on lung tissue exposed to GPEI/GFP plasmid DNA.

FIG. 2 shows the results of immunohistochemical analysis for mouse alveolar macrophages and monocytes having the inventive biopolymer/gene complex delivered thereon.

In "a" and "b" of FIG. 2, the inventive biopolymer/gene complex delivered into the lungs is GPEI/pcDNA3.1-GFP, and in "c" and "d" FIG. 2, the inventive biopolymer/gene complex delivered into the lungs is GPEI/pcDNA 3.1. In "a" and "c" of FIG. 2, signals indicate some GFPs ingested by alveolar macrophages and monocytes, and in "b" of FIG. 2, signals indicate most of GFPs delivered into the lungs.

As shown in FIG. 2, the results of immunohistochemical analysis showed that some of the complexes were ingested by alveolar macrophages or monocytes, but most of the GPEI/GFP DNA complexes were sufficiently delivered into the lung cells.

These results shown in FIG. 2 revealed that the aerosol delivery of the biopolymer/gene complex according to Example 1 effectively acted.

Mode for Invention

EXAMPLE 2

In Vivo Aerosol Delivery of GPEI/DNA Complex 15-week-old K-ras null mice were purchased from Human Cancer Consortium-NCI (Frederick, MD) and accommodated in a breeding chamber maintained at a temperature of 23 ±2° C., a relative humidity of 50±20% and a 12-hr light/12-hr dark cycle. The mice were placed in a nose-only exposure chamber (Dusturbo, Seoul, Korea) (hereinafter, referred to as "NOEC"), and administered with the complex of Example 1 bytheaerosol deliverymethod for about 30 minutes. In this regard, aerosol was generated using a nebulizer (#20304964, Dusturbo). In this Example, a complex containing 1 mg of pcDNA3. 0-PTEN plasmid DNA as described in Example 1 was used. The mice were exposed to the generated aerosol, and after 2 days, mouse lung samples were collected.

EXAMPLE 3

Western Blot Analysis

In order to examine changes in the expression of protein components (e.g., PDK1, Akt1, PTEN, mTOR, 4E-BP1, and p70S6K) of Akt-signaling pathways (e.g., PDK1, Akt1, PTEN, mTOR, 4E-BP1, and p70S6K) in the K-ras null mice exposed to the GPEI/PTEN complex, Western blot analysis was performed in the following manner.

The lung samples collected in Example 2 were homogenized with a lysis buffer (Promega, Madison, Wis.), and the collected proteins were quantified with a Bradford kit (Bio-Rad, Hercules, Calif.). Equal amounts of the proteins were separated on SDS-PAGE and transferred to nitrocellulose membranes (Amersham Pharmacia, Cambridge, UK). Next, the membranes were blocked for 1 hour and incubated with a specific antibody at room temperature for 2 hours. After washing, the membranes were incubated with an HRP-labeled secondary antibody and visualized using a Westzol enhanced chemiluminescence detection kit (Intron, Sungnam, Korea). The bands were detected with LAS-3000 (FUJI-FILM, Tokyo, Japan).

FIG. 3 shows the results of Western blot analysis for Akt proteins, conducted after the delivery of PTEN by the inventive biopolymer/gene complex.

FIG. 3*a* shows the results of Western blot analysis for the expression levels of PTEN, PDK1, Akt1, phospho-Akt (Thr308), phospho-Akt (Ser473) and phospho-mTOR (Ser2448) proteins in PTEN-delivered lung cells. As can be seen in FIG. 3, the expression level of the PTEN protein was increased in the PTEN-delivered mice. In FIG. 3*a*, "C", "V" and "PTEN" indicate a control lung group, a vector control lung group, and a PTEN-delivered lung, respectively.

As can be seen in FIG. 3*a*, the expression level of PTEN was significantly increased in the PTEN-delivered lung cells as compared to the PTEN-nondelivered K-ras and vector control lung groups. On the other hand, the PTEN gene delivery caused a decrease in the expression levels of PDK1, Akt1, phospho-Akt (Thr308), and phospho-mTOR (Ser2448) proteins, but no change in the expression level of phospho-Akt (Ser473).

To examine a change in Akt phosphorylation, the ratio between Akt and phospho-Akt proteins was calculated.

FIG. 3*b* shows the expression levels of Akt in phospho-PTEN. As can be seen in FIGS. 3*b* and 3*c*, the expression level of phospho-Thr308 protein was significantly reduced in a PTEN-delivered lung. However, as can be seen in FIG. 3*d*, the expression level of phospho-Ser473 protein was not changed.

As can be seen in FIGS. 3*b* and 3*c*, the expression levels of total Akt and Thr308 phospho-Akt were significantly lower in the PTEN-delivered lung than in the vector control lung group. As can be seen in FIG. 3*d*, however, the expression level of Ser473 phospho-Akt had no significant change between the vector control group and the PTEN-delivered lung group.

As a result, reductions in the expression levels of PDK1, Akt and Thr308 phospho-Akt were observed in the PTEN-delivered lung, suggesting that PTEN directly regulates the expression of Akt.

FIG. 4 shows the results of regulation of components involved in the Akt signaling pathway.

As can be seen in FIG. 4, the expression levels of 4E-BP1, p70S6K, and cyclin D1 were reduced in a lung into which PTEN has been delivered using the aerosol delivery method by the biopolymer/gene complex according to Example of the present invention. In FIG. 4, "C", "V" and "PTEN" indicate a control group, a vector control group and the PTEN-delivered lung, respectively.

As can be seen in FIG. 4, the aerosol delivery of the PTEN gene significantly reduced the expression levels of p70S6K and cyclin D1 proteins as compared to the control group, and slightly reduced the expression level of 4EBP1 as compared to the control group.

This suggests that the aerosol delivery system according to Example of the present invention caused an increase in the PTEN protein expression level, and this increase is connected with reductions in the activities of proteins involved in the Akt signaling pathway.

Immunoprecipitation and Kinase Assay

A reduction in the phosphorylation of the Akt or mTOR protein is frequently connected with a reduction in kinase activity. In order to examine if this fact is caused by an increase in the PTEN protein level, mTOR and Akt were immunoprecipitated from mouse lung lysate and assayed for kinase activity with their respective substrates, PHAS I and GSK.

The lung samples collected in Example 2 were subjected to the immunoprecipitation of mTOR using the Seize® primary mammalian immunoprecipitation kit (PIERCE, Rockford, Ill.). The assay of mTOR kinase was conducted using 300 μM of ATP and 1 μg off PHAS I (Calbiochem, San Diego, Calif.) for 30 minutes at 30° C. The reaction was terminated by adding 5-fold sample buffer and boiling. The samples were analyzed on 15% SDS/PAGE.

The kinase activity of Akt was assayed with an Akt kinase assay kit (Cell Signaling Technology) according to the manufacturer's instruction.

FIG. 5 shows the results of assays for the kinase activities of p-GSK, Akt, p-4EBP1 and mTOR.

As can be seen in FIG. 5, the kinase activities of the proteins were lower in a PTEN-delivered mouse lung than a control group. In FIG. 5, "C", "V" and "PTEN" indicate the control group, the vector control group, and the PTEN-delivered lung.

As can be seen in FIG. 5, the results showed that the activity of Akt was significantly reduced in the PTEN-delivered mouse lung, but the activity of mTOR was only slightly reduced mTOR.

EXAMPLE 5

Immunohistochemical Analysis

In order to examine the expression levels of Akt and phospho-Akt (Thr and Ser) in the lungs, an immunohistochemical assay was conducted.

The lung samples collected in Example 2 were immediately perfused with ice-cooled 4% phosphate buffered formaldehyde, and post-fixation was performed at room temperature. Then, the lung samples were dehydrated in 30% sucrose overnight and embedded in Tissue-Tek OCT (Sakura, Torrance, Calif.). The lung samples were cut into 5 μm of tissue sections by means of Microtome (Leica, Nussloch, Germany) and mounted on positively charged slides (Fisher, Pittsburgh, Pa.). The lung tissue sections were frozen and incubated in 0.3% hydrogen peroxide (AppliChem, Darmstadt, Germany) for 30 minutes in order to remove the endogenous activity of the frozen sections.

For immunofluorescent staining to determine the efficiency of aerosol gene delivery, the slides were blocked at room temperature for 1 hour to block nonspecific binding sites.

The tissue sections were incubated with a rat anti-mouse macrophage/monocyte antibody (MOMA, SeroTec, Raleigh, N.C.) at 4° C. overnight. On the next day, the tissue sections were washed and incubated with an anti-rat IgG tetramethylrhodamine isothiocyanate-conjugated antibody (Jackson ImmunoResearch West Grove, Pa.) in a dark chamber for one hour.

After washing, the slides having the tissue sections thereon were mounted with coverslips by a fluoromount (BDH, Dorset, UK) and observed under a fluorescent microscope (Carl Zeiss, Thornwood, N.Y.). For the immunohistochemical staining of Akt and p-Akt, the slides was blocked at room temperature for 1 hour to block nonspecific binding sites. The tissue sections were incubated with a primary antibody at 4° C. overnight.

On the next day, the tissue sections were washed and a secondary HRP-conjugated antibody at room temperature for 1 hour. After washing, the tissue sections were incubated in a DAB solution [0.05% 3,3'-diaminobenzidine tetrahydrochloride (Biosesang, Sungnam, Korea) and 0.03% hydrogen peroxide for 5-10 minutes. To label the nuclei, the tissue sections were counterstained with Mayer's hematoxylin (DAKO, Carpinteria, Calif.) and washed with xylene. The slides having tissue sections thereon were mounted with coverslips using Permount (Fisher) and observed under an optical microscope (Carl Zeiss, Thornwood, N.Y.).

FIG. 6 shows the results of immunohistochemical analysis for the phosphorylation of Akt.

In FIG. 6, labeling by incubation is shown in dark brown, and Akt and Thr308 phospho-Akt were expressed at higher levels in vector control mouse lungs (A and D) than in PTEN-delivered mouse lung (B and D). However, the expression of Ser473 phospho-Akt had no difference between the two groups (E and F).

Analysis of Apoptosis

One of potential effects caused by the suppression of the Akt pathway is the induction of apoptosis. In order to examine if PTEN delivered by the aerosol delivery composite according to Example 1 induces apoptosis, vector control lung cells and PTEN gene-delivered lung cells were fixed and subjected to TUNEL assay.

The lung sample tissues collected in Example 2 were placed on slides and fixed on a fixation solution (4% paraformaldehyde in PBS, pH 7.4) and washed with PBS. Then, the lung sample tissues were permeabilized with 0.1% Triton X-100 (0.1% sodium citrate in PBS) on ice for 2 minutes. Then, the slides were washed with PBS, and fragmented DNA ends were labeled using an in situ cell death detection kit (Roche, Basel, Switzerland) by a terminal deoxy-U nick end labeling (TUNEL) method according to the manufacturer's instruction. Finally, the tissue sections were counterstained with methyl green (Trevigen, Gaithersburg, Md.).

FIG. 7 shows the results of the TUNEL analysis.

As can be seen in FIG. 7, apoptosis signals (dark brown) were more clearly detected in the PTEN-delivered lung (B) than in the vector control lung (A).

This suggests that GPEI/PTEN delivered by the aerosol delivery complex functioned to induce apoptosis in vivo, indicating that this gene delivery method can change cellular functions.

While this invention has been described in connection with what is presently considered to be the most practical and preferred embodiment, it is to be understood that the invention is not limited to the disclosed embodiment and the drawings, but, on the contrary, it is intended to cover various modifications and variations within the spirit and scope of the appended claims.

The invention claimed is:

1. A biopolymer/gene complex for the aerosol delivery of a gene construct for the expression of the gene Phosphatase and tensin homolog deleted on chromosome 10 (PTEN), in which the biopolymer comprises glucosylated polyethyleneimine (GPEI) having a substitution of glucose for at least 24 mol % of the primary amino groups of the polyethyleneimine, and the amount of the polyethyleneimine is 2-4 times the amount of the gene construct, and wherein the gene construct is pcDNA3.0-PTEN.

2. The biopolymer/gene complex of claim 1, wherein 30-40 mol % of the primary amino groups in the glucosylated polyethyleneimine (GPEI) are substituted with glucose.

3. The biopolymer/gene complex of claim 2, wherein the primary amino groups are substituted with 18F-FDG.

4. A method for preparing a biopolymer/gene complex for the aerosol delivery of a gene construct for the expression of PTEN, the method comprising: providing a biopolymer including a polyethyleneimine having a substitution of glucose for at least 24 mol % of the primary amino groups of the polyethyleneimine, and binding the desired gene construct to the biopolymer such that the amount of the polyethyleneimine is 2-4 times the amount of the gene construct, wherein the gene construct is pcDNA3.0-PTEN.

5. The method of claim 4, wherein 30-40 mol % of the primary amino groups of the polyethyleneamine (PEI) are substituted with glucose.

6. The method of claim 5, wherein the primary amino groups are substituted with 18F-FDG.

7. A biopolymer/gene complex for the aerosol delivery of a gene construct for the expression of the gene Phosphatase and tensin homolog deleted on chromosome 10 (PTEN), wherein the biopolymer comprises a glycosylated polyethyleneimine in which 30 mol % to 40 mol % of the primary amino groups of the polyethyleneimine have been substituted with fluorine 18 fluorodeoxyglucose (18F-FDG), wherein the amount of the polyethyleneimine is 2-times to 4-times the amount of the gene construct, and wherein the gene construct is pcDNA3.0-PTEN.

8. A biopolymer/gene complex for the aerosol delivery of a gene construct for the expression of the gene Phosphatase and tensin homolog deleted on chromosome 10 (PTEN), in which the biopolymer comprises glucosylated polyethyleneimine (GPEI) having a substitution of glucose for at least 24 mol % of the primary amino groups of the polyethyleneimine, and the amount of the polyethyleneimine is 2-4 times the amount of the gene construct, wherein the gene construct is pcDNA3.0-PTEN, and wherein said biopolymer/gene complex expresses PTEN and decreases Akt expression in transfected cells.

* * * * *